(12) United States Patent
Lash et al.

(10) Patent No.: US 12,232,933 B2
(45) Date of Patent: Feb. 25, 2025

(54) DRESSING FOR PROVIDING LOW OXYGEN ENVIRONMENT

(71) Applicant: Advanced Dressing, LLC, Cleveland, OH (US)

(72) Inventors: Thomas E. Lash, Chardon, OH (US); Timothy Wojciechowski, Westlake, OH (US); John Buan, Maple Grove, MN (US); Richard L. Middaugh, Rocky River, OH (US); Edward B. Armstrong, Chagrin Falls, OH (US)

(73) Assignee: ADVANCED DRESSING, LLC, Cleveland, OH (US)

( * ) Notice: Subject to any disclaimer, the term of this patent is extended or adjusted under 35 U.S.C. 154(b) by 566 days.

(21) Appl. No.: 17/624,635

(22) PCT Filed: Jul. 29, 2020

(86) PCT No.: PCT/US2020/043950
§ 371 (c)(1),
(2) Date: Jan. 4, 2022

(87) PCT Pub. No.: WO2021/021851
PCT Pub. Date: Feb. 4, 2021

(65) Prior Publication Data
US 2022/0257422 A1    Aug. 18, 2022

Related U.S. Application Data

(60) Provisional application No. 62/880,317, filed on Jul. 30, 2019.

(51) Int. Cl.
*A61F 13/00*    (2024.01)
*A61B 46/20*    (2016.01)
(Continued)

(52) U.S. Cl.
CPC ........ *A61F 13/00063* (2013.01); *A61B 46/20* (2016.02); *A61F 13/05* (2024.01);
(Continued)

(58) Field of Classification Search
CPC .............. A61F 13/00063; A61F 13/05; A61F 13/00072; A61F 13/0233; A61B 46/20;
(Continued)

(56) References Cited

U.S. PATENT DOCUMENTS 5,158,537 A    10/1992    Haak
5,288,289 A    2/1994     Haak
(Continued)

FOREIGN PATENT DOCUMENTS

JP    2013090956 A    5/2013
JP    2018535808 A    12/2018
(Continued)

OTHER PUBLICATIONS

International Search Report filed in PCT/US20/43950 mailed Oct. 20, 2020.
(Continued)

*Primary Examiner* — Andrew J Mensh
*Assistant Examiner* — Meagan Ngo
(74) *Attorney, Agent, or Firm* — Rankin, Hill & Clark LLP

(57) ABSTRACT

A dressing includes an application site covering and an oxygen scavenger provided with or positioned with respect to the application site covering so as to remove oxygen from a volume beneath the application site covering and around an application site covered by the application site covering. The application site covering and the oxygen scavenger are configured to maintain gas pressure beneath the application site covering around the application site that is above a
(Continued)

therapeutic negative pressure while the oxygen scavenger is consuming oxygen beneath the application site covering.

18 Claims, 6 Drawing Sheets

(51) Int. Cl.
 *A61F 13/05*  (2024.01)
 *A61M 1/00*  (2006.01)
 *B01J 20/04*  (2006.01)
 *B01J 20/26*  (2006.01)
 *B01J 20/28*  (2006.01)

(52) U.S. Cl.
 CPC ............ *A61M 1/962* (2021.05); *B01J 20/046* (2013.01); *B01J 20/26* (2013.01); *B01J 20/2803* (2013.01); *B01J 20/28035* (2013.01)

(58) Field of Classification Search
 CPC ........ A61M 1/962; B01J 20/046; B01J 20/26; B01J 20/2803; B01J 20/28035; A61L 2300/10; A61L 15/58; A61L 15/44
 See application file for complete search history.

(56) References Cited

U.S. PATENT DOCUMENTS

| | | | |
|---|---|---|---|
| 6,875,400 | B2 | 4/2005 | Speer |
| 10,046,095 | B1* | 8/2018 | Middaugh ............. A61M 1/962 |
| 2005/0070835 | A1* | 3/2005 | Joshi ..................... A61M 1/962 |
| | | | 602/41 |
| 2018/0021178 | A1* | 1/2018 | Locke ................. A61F 13/0206 |
| | | | 602/43 |
| 2018/0318165 | A1* | 11/2018 | Donda ................ A61H 9/0071 |
| 2019/0091382 | A1 | 3/2019 | Middaugh |
| 2020/0069479 | A1 | 3/2020 | Buan |
| 2022/0087870 | A1* | 3/2022 | Pratt ................... A61F 13/0243 |

FOREIGN PATENT DOCUMENTS

| | | |
|---|---|---|
| WO | 2009/145894 | 12/2009 |
| WO | 2017/075381 | 5/2017 |

OTHER PUBLICATIONS

Supplemental EP Search Report filed in EP 20 84 7561 dated Apr. 11, 2023.

* cited by examiner

DRESSING FOR PROVIDING LOW OXYGEN ENVIRONMENT

BACKGROUND

Oxygen scavengers are known for use in negative pressure wound therapy. For example, US 2005/0070835 A1 discloses a device and method for creating a negative partial pressure including a gas or fluid impermeable housing where an oxygen absorber/remover is positioned within the cavity. WO 2017/075381 A1 also discloses a wound therapy device that includes a reactor than can scavenge oxygen.

US 2005/0070835 A1 discusses how the device includes a housing that is preferably constructed from a rigid or semi-rigid type material. US 2005/0070835 A1 mentions different types of oxygen absorbers such as those that absorb oxygen through the oxidation of iron metal. US 2005/0070835 A1 further mentions silver oxide, metal peroxides, silver metal, and antimicrobial organic compounds. Placing these types of oxygen absorbers in the cavity formed by a gas or fluid impermeable housing to cover a wound would result in no oxygen (or a nearly undetectable amount) within the cavity unless the reacting agent in the oxygen scavenger was specifically designed to limit the amount of oxygen scavenged within the cavity, which US 2005/0070835 A1 does not discuss in any particularity.

WO 2017/075381 A1 discusses how the reactor can consume oxygen, which may result in an approximate 20% reduction from atmospheric pressure in an enclosed volume around a wound.

The range of negative pressures currently used for popularly available negative pressure wound therapy (NPWT) systems is in the range of about −5% to about −20% of atmospheric pressure, or about −40 mmHg to about −150 mmHg from atmospheric pressure. A negative pressure of less than −5% (about −40 mmHg) could be considered to be outside the range of therapeutic negative pressure, and there may be instances, where removing oxygen from around the wound may be desirable, but the need for typical therapeutic negative pressure ranges may not be necessary.

SUMMARY

In view of the foregoing, a dressing includes an application site covering and an oxygen scavenger provided with or positioned with respect to the application site covering so as to remove oxygen from a volume beneath the application site covering and around an application site covered by the application site covering. The application site covering and the oxygen scavenger are configured to maintain gas pressure beneath the application site covering around the application site that is above a therapeutic negative pressure while the oxygen scavenger is consuming oxygen beneath the application site covering.

DETAILED DESCRIPTION

Figure 1:
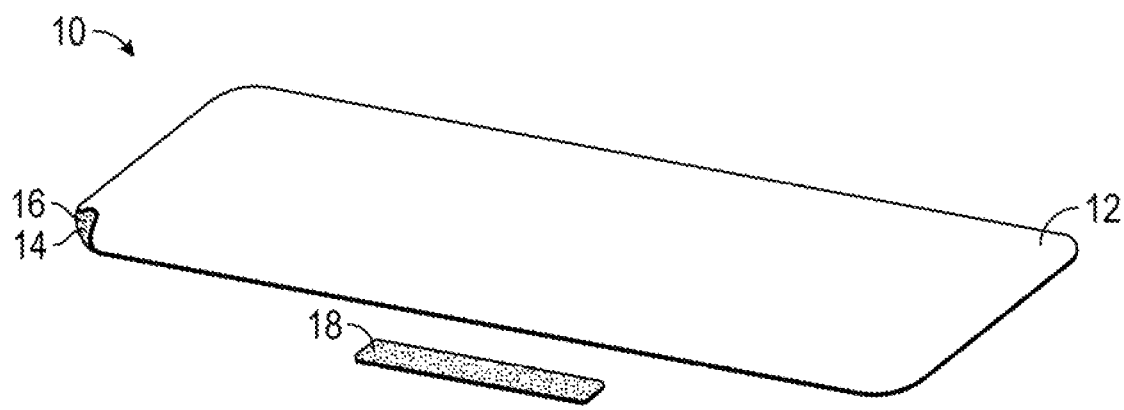
FIG. 1 is an exploded view of a dressing.
Figure 2:
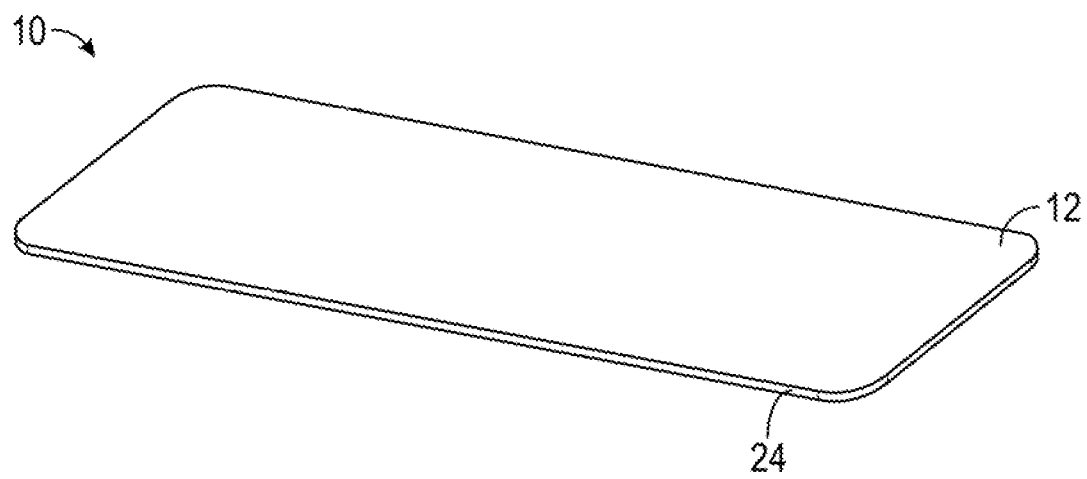
FIG. 2 is another exploded view of a dressing.

FIG. 1 depicts a dressing 10 including an application site covering in the form of a drape 12, an adhesive 14 on a skin-facing surface 16 of the drape 12 and an oxygen scavenger 18. FIG. 2 depicts an application site covering in the form of two films where an oxygen scavenger is incorporated in a film-forming polymer that is used to make the oxygen scavenger film 24, which is applied to the drape 12. In each instance, the oxygen scavenger 18 or the oxygen scavenger incorporated into the oxygen scavenger film 24 is designed to react with gaseous oxygen ($O_2$), removing it from any air that is in contact with the oxygen scavenger. With the dressing 10 sealed to the skin, this results in a topical hypoxic or very low oxygen environment around an application site covered by the application site covering, which can be beneficial for certain skin conditions. Accordingly, the oxygen scavenger can be provided with or positioned with respect to the application site covering so as to remove oxygen from a volume beneath the application site covering and around an application site covered by the application site covering. As will be described in more detail below, the application site covering and the oxygen scavenger are configured to maintain gas pressure beneath the application site covering around the application site that is above the therapeutic negative pressure discussed above. The dressing is configured so that the gas pressure beneath the dressing is at atmospheric pressure or nearer to atmospheric pressure as compared to one used in a typical NPWT system.

Figure 3:
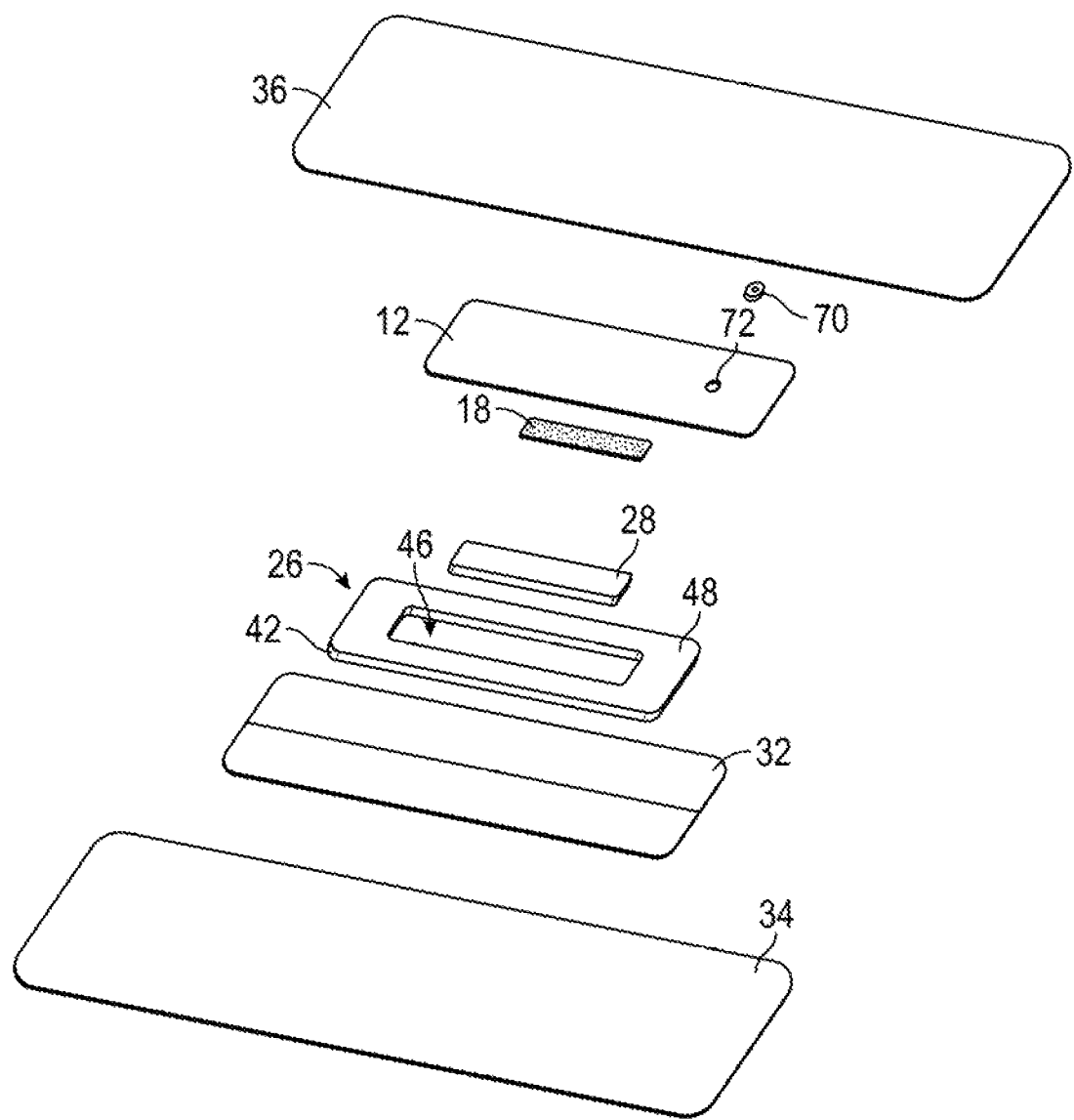
FIG. 3 is another exploded view of a dressing.
Figure 4:
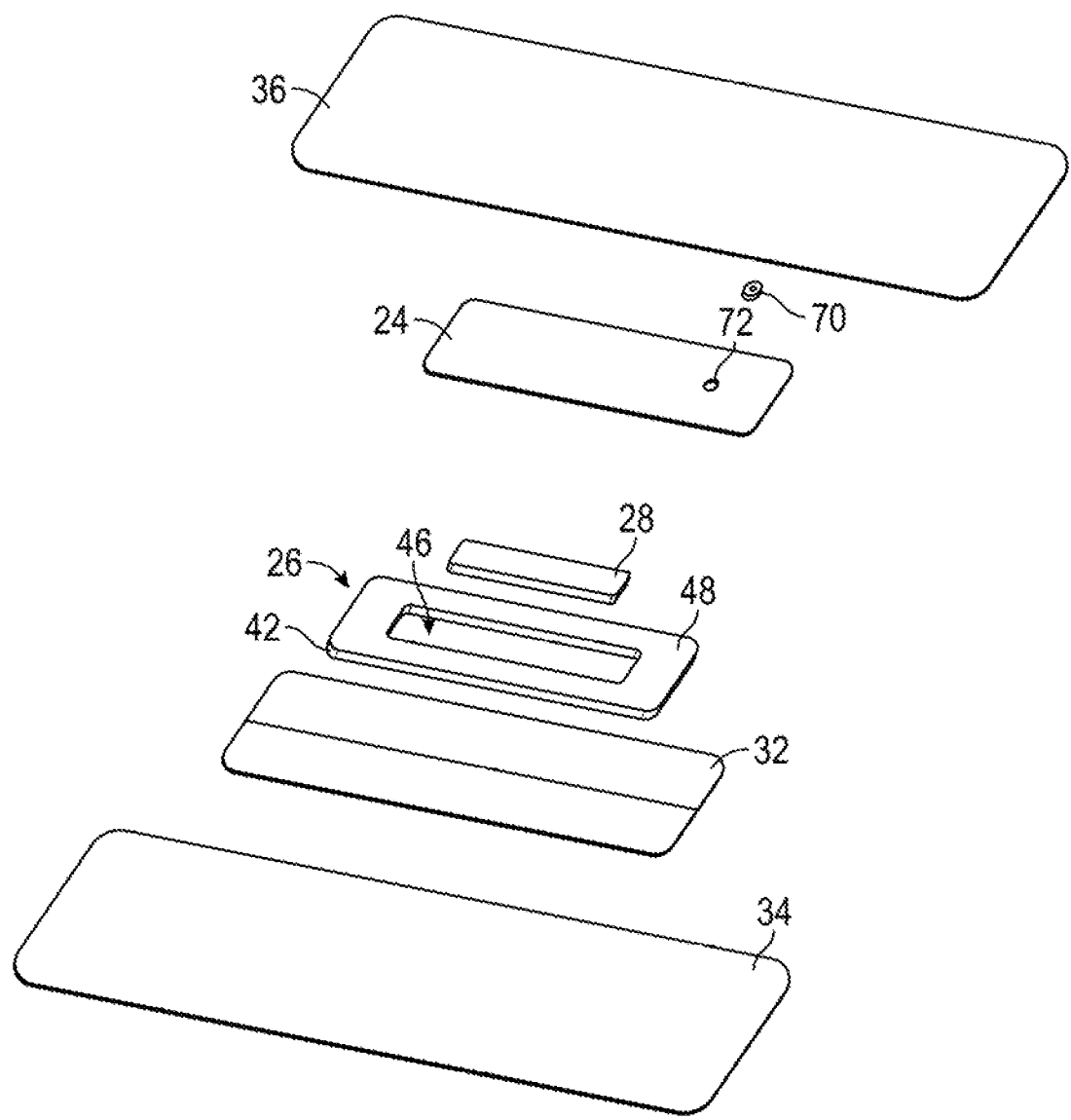
FIG. 4 is another exploded view of a dressing.

FIGS. 3 and 4 depict a gasket 26, wicking material 28, and a release layer 32, which can also be provided with the dressing 10. FIG. 3 also depicts a sealed package, which can be made up of a lower foil layer 34 and an upper foil layer 36 that can be affixed to one another, in which the dressing 10, when assembled, is sealed. The sealed package inhibits ambient oxygen from reacting with the oxygen scavenger until after the dressing 10 has been removed from the sealed package. FIG. 4 depicts the application site covering being made from the oxygen scavenger film 24 described above.

The drape 12 may be made from a flexible material and can be made from a thin, flexible elastomeric film. Unlike a rigid or semi-rigid type gas or fluid impermeable housing, the drape 12 (and other application site coverings) are conformable to the wicking material 28 and skin to which it is applied. Examples of such materials include polyurethane or polyethylene films. The thin film from which the drape 12 is made can be substantially impermeable to liquids but somewhat permeable to water vapor and other gases. For example, the thin film material from which the drape 12 is made may be constructed of polyurethane or other semi-permeable material such as that sold under the Tegaderm® brand or 9834 TPU tape available from 3M. Similar films are also available from other manufacturers.

FIG. 2 depicts the oxygen scavenger film 24 applied to the drape 12. The oxygen scavenger film 24 can be made in accordance with the teachings of U.S. Pat. No. 7,781,018 B2 or the patent documents discussed therein. If desired, the oxygen scavenger film 24 can be provided as the application site covering itself, which is shown in FIG. 4 and can be made in accordance with the teachings of U.S. Pat. No. 7,781,018 B2 or the patent documents discussed therein. In either instance, the oxygen scavenger film 24 acting as the drape or the oxygen scavenger film 24 applied to the drape 12, the oxygen scavenger film 24 or the drape 12 in combination with the oxygen scavenger film 24 results in a film or films that is as flexible or nearly as flexible as films sold under the Tegaderm® brand or 9834 TPU tape available from 3M. The oxygen scavenger film 24 could also be conformable to the wicking material 28 and skin to which it is applied. This conformability of the application site covering, whether it be the drape 12 or the oxygen scavenger film 24, can allow for the application site covering to be drawn toward the skin as oxygen is being removed from beneath the application site covering, which allows for volume reduction beneath the application site covering.

With reference to FIG. 3, the gasket 26 can include silicone 42 such as a polysiloxane gel adhesive with good moisture and gas barrier properties, such as P-DERM PS-1050 from Polymer Science, Inc. The gasket 26, which can include an inner through hole 46, is formed by providing the silicone 42 on a gasket backing film 48, which can be a polyurethane, polyethylene, polypropylene, or co-polyester film. The gasket backing film 48 can be brought in contact with the adhesive 14 on a skin-facing surface 16 of the drape 12 to affix the gasket 26 to the drape. The gasket 26 can attach to the oxygen scavenger film 24 in similar manners. A variation on gasket constructions can include using a hydrogel instead of silicone as the gasket. Other materials that provide a better seal than acrylic adhesives against skin can also be used as the gasket.

One example of the oxygen scavenger 18 for use in the embodiment depicted in FIG. 1 is a porous composite of zinc powder (Zn), carbon powder (C), potassium bromide (KBr), and a binder such as polyfluoroethylene (PTFE), with or without added water ($H_2O$) similar to a Rechargeable Battery Company (dba Exothermix) Air Activated Heater. Another variation is an oxygen scavenger including a reactive material from iron fines, or any other material that can react with 02 present at the application site covered by the drape 12 and absorbing it when in contact after activation.

Figure 5:
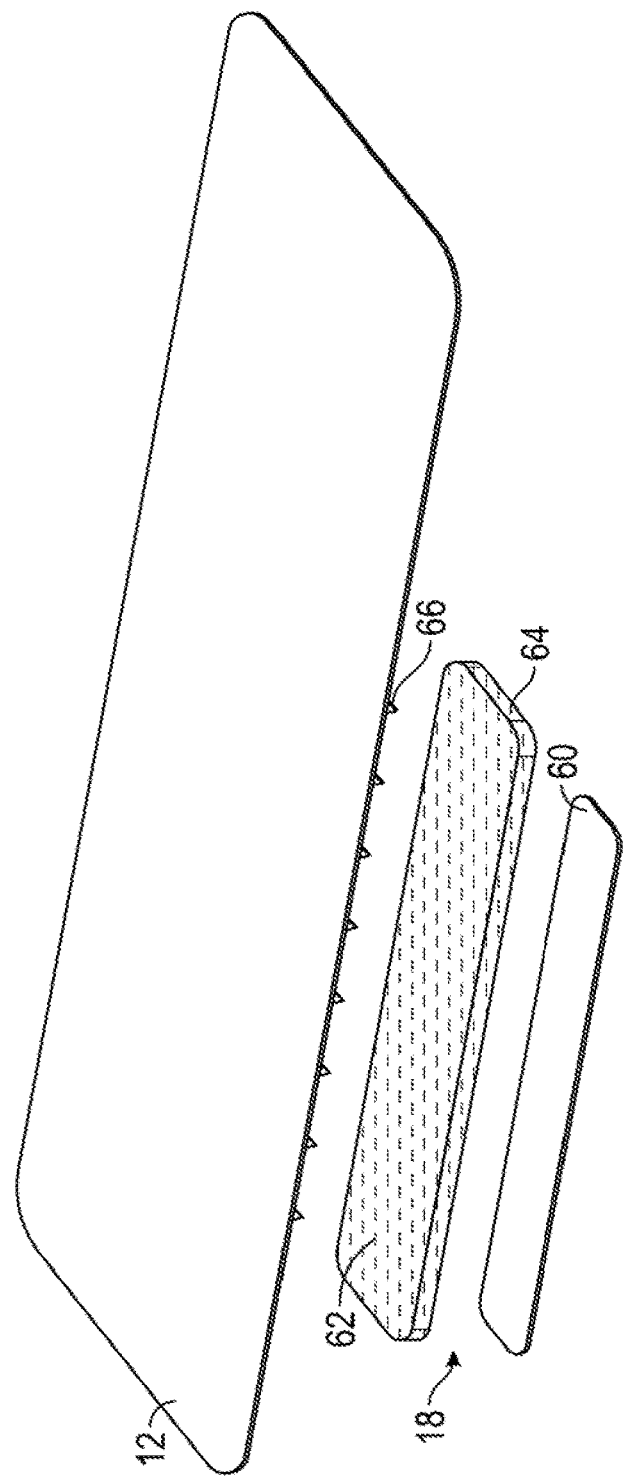
FIG. 5 is another exploded view of a dressing.

FIG. 5 depicts the oxygen scavenger 18 where the reducing agent, which can include aluminum, zinc or iron, can be provided on, e.g., printed on, a thin substrate, hereinafter referred to as the reducing agent substrate 60. An electrolyte solution 62, which can be provided in a rupturable package 64, is shielded from the reducing agent substrate 60, and thus the reducing agent, until the dressing 10 is ready to be placed on the skin obviating the need for a hermetically sealed package to contain the dressing 10. Small protuberances 66, which can be similar in shape and size to solid microneedles used in touch-actuated microneedle array patches, can be fixed to or provided below (relative to the application site) the skin-facing surface 16 of the drape 12. The small protuberances 66 can be used to rupture the rupturable package 64 so that the electrolyte solution 62 is introduced to the reducing agent on the reducing agent substrate 60. One presses on the drape 12 in the vicinity of the protuberances to rupture the rupturable package 64. The rupturable package 64 can be ruptured in other manners.

With reference back to FIGS. 3 and 4, the wicking material 28 can be any appropriate material with the capability of removing moisture from the skin. In certain instances, however, the wicking material 28 can be configured to shrink when atmospheric pressure pushing on the drape 12 exceeds an internal air pressure beneath the drape 12 and around an application site covered by the drape plus a mechanical compression resistance pressure of the wicking material. This will be described in more detail below.

The adhesive 14 may be a pressure-sensitive acrylic-based adhesive applied on the skin-facing surface 16 of the drape 12. Other types of adhesives could be applied to the drape 12, for example, a photoresponsive adhesive polymer such as those described in U.S. Pat. No. 10,336,923 B2. A pressure-sensitive acrylic-based adhesive is known to provide strong initial tack that can last for a relatively long time, for example a few days, when in contact with the skin. The adhesive 20 can be applied over an entirety of the skin-facing surface 16 of the drape 12, which can also be useful to retain other components of the dressing 10 during assembly. Known pressure-sensitive acrylic-based adhesives, however, are not known for providing a good seal so as to preclude or greatly inhibit the ingress and egress of air, thus the gasket 26 in addition to the adhesive 14 can be provided with the dressing 10.

The release layer 32 protects the gasket 26 and the adhesive 14 until ready for application to the application site, e.g., a patient's skin. The release layer 32 can be coated with a fluoropolymer release coating on the side of the release layer 32 that contacts the adhesive 14 on the drape 12 and the appropriate surfaces of the gasket 26 and the wicking material 28. The release layer 32 can be a polyester film coated on one side with the fluoropolymer release coating, which can be used with silicone. This release coating is also compatible with pressure-sensitive acrylic-based adhesives. The release layer 32 has a larger area than the drape 12 and is removed from the drape 12 prior to the drape being affixed to application site.

The drape 12, oxygen scavenger 18, gasket 26, wicking material 28, and release layer 32 can be assembled in different manners in the dressing 10. Additionally, there are different manners in which the oxygen scavenger 18 might be formulated including: (1) with a reducing agent, e.g., zinc, iron, aluminum, and an electrolyte solution needed to support the reaction of the reducing agent with oxygen, (2) with the reducing agent and an electrolyte salt but not the solvent water so there is no electrolyte solution, or (3) with the reducing agent but without either the electrolyte salt or solvent water.

When the reducing agent is provided with the electrolyte solution, the oxygen scavenger 18 is in an activated state and must be protected from contact with air until use. At the time of use, the dressing 10 is removed from its protective packaging (shown in FIG. 3 as the lower foil layer 34 and the upper foil layer 36) and applied quickly to the application site. The protective packaging can be, for example, a sealed metallized, e.g., foil-type, package that precludes air from entering the package until after opened. After the dressing 10 is removed from the protective packaging, the oxygen scavenger 18 begins immediately to remove oxygen from the air. With the dressing 10 being applied quickly to the application site, the oxygen scavenger 18 removes oxygen from the air trapped between the dressing 10 and the skin, and achieves an oxygen-free or nearly oxygen-free environment in minutes to hours. Ease of use is simplest, but requires swift application of the dressing 10 after opening its packaging. The drape 12 and the gasket 26 provide an adequate barrier to slow $O_2$ permeation to the oxygen scavenger 18 from the external environment, so that the main access of $O_2$ to the reducing agent is through the wicking material 28 from the trapped air within the dressing 10 sealed to the skin. This produces the desired oxygen-free or nearly oxygen-free environment on the skin within the area bounded by the gasket 26.

If the oxygen scavenger 18 includes an electrolyte salt (such as KBr) but not solvent water, it will not be in an active state until water is added. The oxygen scavenger 18, and thus the dressing 10, will need to be protected from moisture vapor, but oxygen exclusion will not be important. The water addition could be drops of water, contact with perspiration on the skin, or even condensation of water vapor from the humidity in the trapped air driven by moisture vapor from the skin, since the electrolyte salt can be expected to be deliquescent. Use requires addition of water, which is readily available in most environments. Timing between opening the dressing package and applying the dressing 10 to the target skin is less critical than in the case of the oxygen scavenger 18 being active as packaged. The solvent water could also be provided in a rupturable package similar to the rupturable package 64 shown in FIG. 5.

If the oxygen scavenger 18 does not include an electrolyte salt or solvent water, an electrolyte solution must be added at the time of use to enable the oxygen scavenger 18 to react with oxygen in the air. If the period of use of the dressing 10 is short enough, a solution of table salt could activate the oxygen scavenger 18 without causing rapid corrosion of an active component of zinc. This would not require complete protection of the oxygen scavenger 18, and thus the dressing 10, from exposure to air or moisture.

Removal of $O_2$ from an enclosed volume of air reduces its pressure. In a rigid container, removal of $O_2$ would cause a 20% reduction in pressure (assuming some humidity). However, comfortable dressing materials are not rigid, and typical wicking materials are compressible, so the volume of trapped air will shrink when the internal air pressure is less than the external air pressure. This shrinkage in air volume restores at least part of the pressure lost by the removal of $O_2$. Applying the ideal gas law equation to the nitrogen only and specifying that $P_{N2, before\ shrinkage} = P_{N2, atm}$:

$$P_{N2,atm} V_{before\ shrinkage} = P_{N2, after\ shrinkage} V_{after\ shrinkage}, \text{ or}$$

$$P_{N2, after\ shrinkage} = (V_{before\ shrinkage}/V_{after\ shrinkage}) P_{N2, atm}$$

If there is no resistance to wicking material air volume shrinkage, then $$\text{Negative pressure } NP = P_{atm} - P_{N2, after\ shrinkage}$$

$$NP = P_{atm} - P_{N2, atm}(V_{before}/V_{after})$$

However, the wicking material 28 will have resistance to the compression required to shrink the air volume. The dressing 10 will shrink until there is a balance between the atmospheric pressure pushing down on the drape 12 (or outermost material of the dressing 10, for example, when an drape 12 is not provided) and the combination of internal air pressure and the mechanical compression resistance pressure of the wicking material 28.

$$P_{atm} = P_{N2, after} + P_{mechanical\ compression\ resistance}$$

The internal dressing air pressure will be determined by the compressibility of the wicking material 28. The more easily compressed the wicking material 28 (lower $P_{mechanical}$), the closer $P_{N2, after}$ will be to $P_{atm}$ and the less negative air pressure will be beneath the dressing 10:

$$\text{Negative Pressure } (NP) =$$
$$P_{atm} - P_{N2, after} = (P_{N2, after} + P_{mechanical}) - P_{N2, after}$$
$$NP = P_{mechanical\ compression\ resistance}$$

Since the $O_2$ removed from the dressing 10 air represents only 20% of its air, the air volume beneath the dressing 10 cannot shrink more than 20% under the influence of atmospheric pressure. At 20% shrinkage, the remaining $N_2$ pressure beneath the dressing 10 would be equal to the total atmospheric pressure $P_{atm}$.

The range of negative pressures currently used for popularly available negative pressure wound therapy systems is in the range of $-60$ mmHg to $-150$ mmHg, or $-8\%$ to $-20\%$ of atmospheric pressure. A negative pressure of 5% ($-40$ mmHg) or less could be considered to be outside the range of therapeutic negative pressures.

A wicking material "spongy" enough that up to 40 mmHg of external pressure would compress its air volume by 20% would produce an atmosphere of $N_2$ at under the dressing 10 at a pressure equal to or less than 40 mmHg below atmospheric pressure.

$$\text{Initial state:} P_{atm} V_{before\ shrinkage} = (n_{N2} + n_{O2})RT = P_{N2, atm} + P_{O2, atm}$$

$$\text{After removal of } O_2: P_{N2, atm} V_{before\ shrinkage} = n_{N2} RT$$

$$\text{After shrinkage:} P_{N2, patch} V_{after\ shrinkage} = n_{N2} RT$$

Negative pressure: $(NP) =$ $$P_{atm} - P_{N2, patch} = P_{atm} - n_{N2} RT/V_{after\ shrinkage}$$

$$NP = P_{atm} - P_{N2, atm} V_{before\ shrinkage}/V_{after\ shrinkage}$$

For $NP = 5\%$ of $P_{atm}: 0.05 P_{atm} = P_{atm} - P_{N2, atm} V_{before}/V_{after}$ Knowing $P_{N2, atm} = 0.80 P_{atm}: 0.05 P_{atm} = P_{atm} - 0.80 P_{atm} V_{before}/V_{after}$ $$V_{before}/V_{after} = 0.95 P_{atm}/0.80 P_{atm} = 1.1875$$

Shrinkage as fraction of starting volume =

$$(V_b - V_a)/V_b = 1 - V_a/V_b = 1 - (1/1.1875) = 1 - 0.84 = 0.16 = 16\%$$

In other words, a wicking material whose air volume can be compressed 16% by 40 mmHg of pressure could produce an environment beneath the dressing 10 free of $O_2$ with a negative pressure of 40 mm Hg.

For an open-pore wicking material whether fibrous or foam, the material from which the wicking material 28 is made is chosen to have its air volume compressed by 16% or more at 40 mmHg pressure to make a dressing 10 with up to 40 mmHg negative pressure beneath the dressing 10.

If the wicking material 28 starts at about 80% porous, compressing 16% of 80% would require compressing the bulk dimensions by only 13%. If the wicking material 28 starts at about 60% porous, compressing 16% of that 60% would require compressing the bulk dimensions by only 10%.

Figure 6:
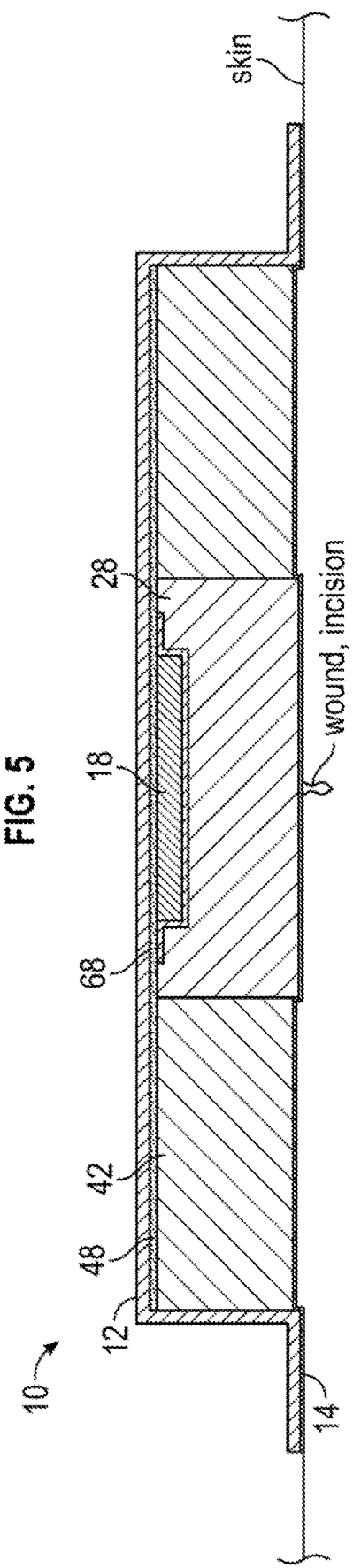
FIG. 6 is a schematic cross-sectional view of the dressing of FIG. 3.

The dressing 10 can be assembled in different manners. In one example and with reference to FIGS. 3 and 6, the drape 12 can be flood coated on the skin-facing surface 16 with the adhesive 14. The gasket 26, which can include the inner through hole 46, can be attached to the drape 12 by providing the silicone 42 on the gasket backing film 48, which can be a polyurethane, polyethylene, polypropylene, or co-polyester film. The gasket backing film 48 is brought in contact with the adhesive 14 on the skin-facing surface 16 of the drape 12. The oxygen scavenger 18, which can be deposited or printed onto a carrier film, can be positioned within the through hole 46 in the gasket 26. The carrier film for the oxygen scavenger 18 is brought in contact with the adhesive 14 on the skin-facing surface 16 of the drape 12. If desired, a liquid-impermeable but gas-permeable membrane 68 can be provided between the oxygen scavenger 18 and the wicking material 28. The wicking material 28, which is larger in area that the carrier film for the oxygen scavenger 18, is also brought in contact with the adhesive 14 on the skin-facing surface 16 of the drape 12. The release layer 32 is then brought in contact with the adhesive 14 on the skin-facing surface 16 of the drape 12 to cover also the gasket 26 and the wicking material 28 to provide the assembled dressing 10.

Figure 7:
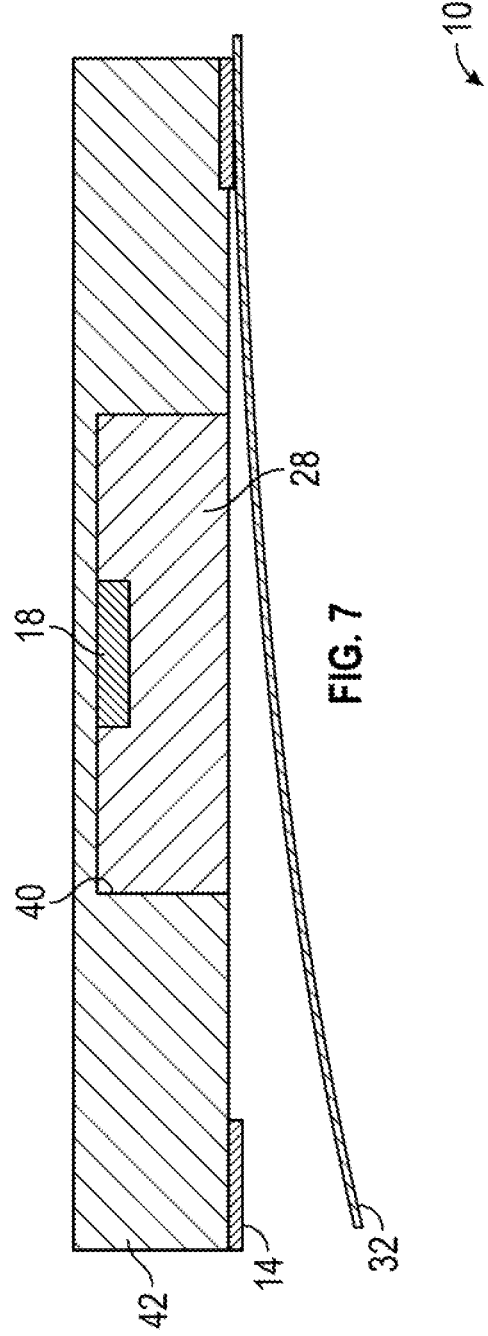
FIG. 7 is a schematic cross-sectional view of a dressing.

The dressing 10 could also be assembled without the drape 12 or the application site covering in the form of the oxygen scavenger film 22, an example of which is shown in FIG. 7. In this construction, the application site covering can be in the form the silicone 42, which does not include a through hole, but instead includes a cavity 40 to allow the silicone 42 to receive while covering the oxygen scavenger 18 and the wicking material 28 with respect to ambient atmosphere. The oxygen scavenger 18, which can be printed or deposited on a thin carrier film, is placed in the cavity 40 in the silicone 42 and then is covered with the wicking material 28. Adhesive 14, which may or may not be provided on a carrier film similar to the gasket backing film 48 described above, can be provided around the perimeter of the silicone 42 to facilitate adhesion of the dressing 10 to the skin. The release layer 32 is then brought in contact with the adhesive 14 to cover also the silicone 42 and the wicking material 28 to provide the assembled dressing 10.

Figure 8:
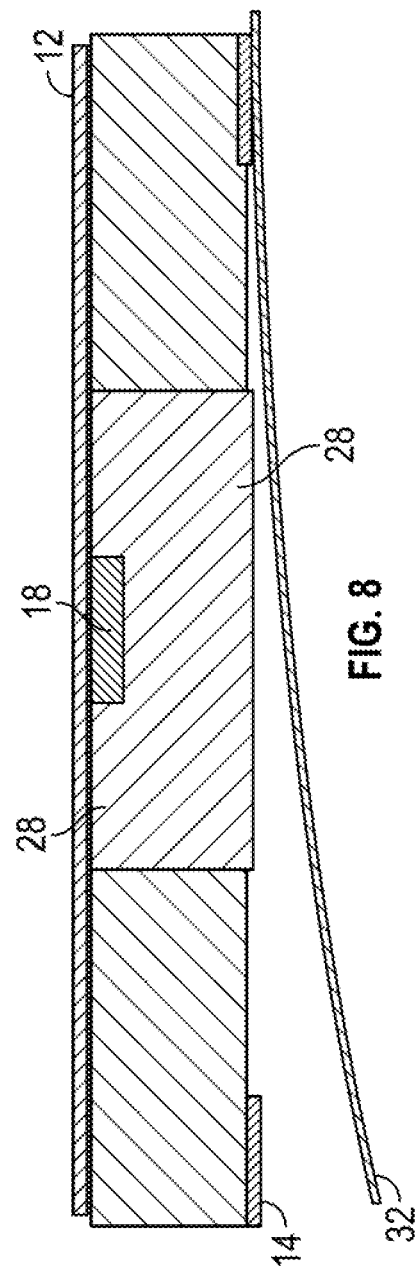
FIG. 8 is another schematic cross-sectional view of a dressing.

The dressing 10 could also be assembled where the drape 12 does not contact the skin, but rather provides a carrier for stacking the components that make up the dressing 10. Such an example is shown in FIG. 8.

A variation on the dressing constructions described above include using a hydrogel instead of the silicone 42 to establish a seal to the skin. The electrolyte and reducing agent, with or without the PTFE, could be mixed into the hydrogel. Use of a hydrogel would require moisture barrier packaging to preserve the water content of the hydrogel.

The speed with which the oxygen tension decreases under the dressing 10 can be slowed by interposing an oxygen permeable membrane between the wicking material 28 and the oxygen scavenger 18 or between the wicking material 28 and the skin. Combining an oxygen permeable membrane between wicking material 28 and oxygen scavenger 18, accompanied by an oxygen permeable drape over the part of the wicking material 28 not covered by the oxygen scavenger 18 would allow a non-zero $O_2$ level on the skin.

In another alternative and with reference to FIGS. 3 and 4, a valve 70 can be provided with the drape 12 or the oxygen scavenger film 24 and cooperate with an opening 72 provided in each. The valve 70 can be similar in construction to that described in EP 1 958 883 B1. Operation of the valve 70 will be described in detail with reference to the drape 12 with the understanding that the valve would operate similarly with the oxygen scavenger film 24. The valve 70 can be configured to open and allow air into the volume beneath the drape 12 to allow the volume beneath the drape 12 to maintain gas pressure beneath the drape 12 above a therapeutic negative pressure, and preferably nearer to atmospheric pressure than to the therapeutic negative pressure. For example, the valve 70 can be configured to open at a pressure differential between the volume beneath the drape 12 and ambient at less than −60 mmHg or even less than −40 mmHg. As such, when the valve 70 is open, air enters through the valve 70 and the opening 72 into the volume beneath the drape 12 raising the gas pressure towards ambient atmospheric pressure. The system will then equilibrate dynamically to a nearly pure nitrogen atmosphere at nearly atmospheric pressure. A mechanical pump could be inserted into or over the top of the valve 70 to remove air under the patch to reduce the pressure to −1 to −40 mmHg.

Figure 9:
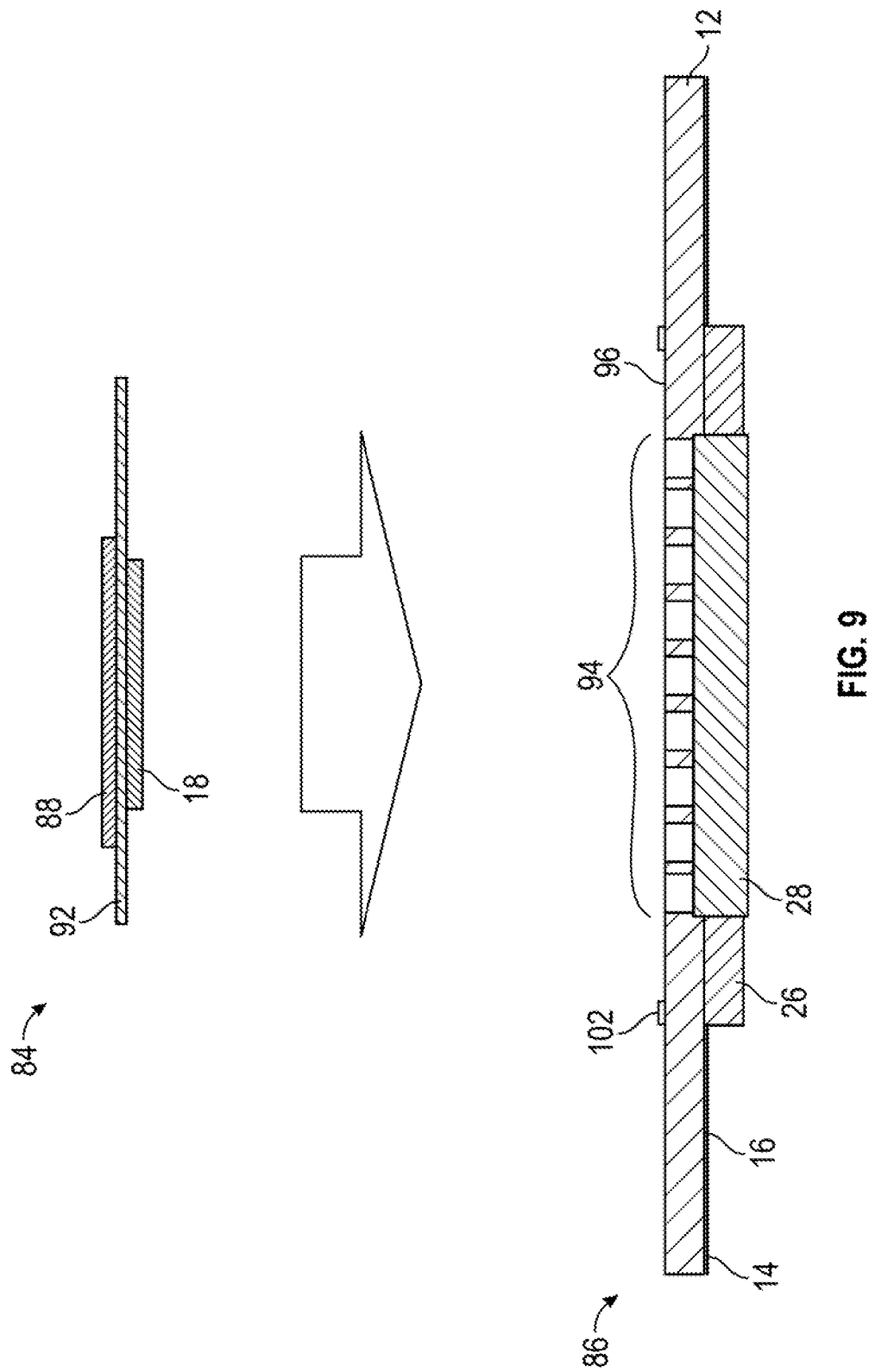
FIG. 9 is another schematic cross-sectional view of a dressing.

FIG. 9 depicts a two-piece dressing having a top assembly 84 and a bottom assembly 86. The bottom assembly 86 includes the drape 12, the gasket 26, the wicking material 28 and adhesive 14 on the skin-facing surface 16 of the drape 12. The wicking material 28 can be an anti-microbial pad, which could also hold the water or electrolyte solution to activate the reducing agent of the oxygen scavenger 18. The wicking material 28 may also include a layer of silver, which is not shown. The top assembly 84 includes the oxygen scavenger 18, which can be printed or deposited on a thin flexible carrier 88 having an adhesive layer 92, e.g., tape. Also, the oxygen scavenger 18 could be any of the aforementioned oxygen scavengers. The oxygen scavenger 18 can be packaged in an active state within a sealed package (for example, similar to the foil layers 34, 36) so to have depleted the oxygen in the sealed package before being applied and adhered to the drape 12.

After the bottom assembly 86 is applied over the application site, the top assembly 84 is applied over the bottom assembly 86. To apply the top assembly 84, lay the top assembly 84 top-down on a surface. Remove a release liner (not shown) to expose the adhesive layer 92 and the oxygen scavenger 18. Position the top assembly 84 over a porous or perforated area 94 of the drape 12 and adhere the adhesive layer 92 to an outer surface 96 of the drape 12. The porous or perforated area 94 of the drape 12 is confined within the area bound by the gasket 26 beneath the drape 12 and the top assembly 84 covers the porous or perforated area 94 of the drape 12 when properly applied and adhered to the drape 12. Alignment marks 102 that remain visible when the top assembly 84 is adhered to bottom assembly 86 can be provided on the outer surface of the drape 12. The top assembly 84 and the bottom assembly 86 can be individually packaged, and top assembly 84 could be replaced as required without removing the bottom assembly 86.

It will be appreciated that various features and functions of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:
1. A dressing comprising:
an application site covering;
an oxygen scavenger provided with or positioned with respect to the application site covering so as to remove oxygen from a volume beneath the application site covering and around an application site covered by the application site covering, the application site covering and the oxygen scavenger being configured to maintain gas pressure beneath the application site covering around the application site that is above a therapeutic negative pressure while the oxygen scavenger is consuming oxygen beneath the application site covering; and a wicking material that is configured to shrink when atmospheric pressure pushing on the application site covering exceeds an internal air pressure beneath the application site covering and a mechanical compression resistance pressure of the wicking material.

2. The dressing of claim 1, wherein the application site covering is a drape made from a film, and further comprising an adhesive disposed on a skin-facing surface of the drape.

3. The dressing of claim 2, wherein the oxygen scavenger is coupled to the drape via the adhesive.

4. The dressing of claim 2, further comprising a gasket disposed on the skin-facing surface of the drape, wherein the gasket includes silicone, the dressing further comprising a gasket backing film upon which the silicone is provided, and the gasket backing film is coupled to the drape via the adhesive.

5. The dressing of claim 1, wherein the oxygen scavenger is incorporated in a film-forming polymer that is used to make the application site covering or an oxygen scavenger film that is applied to the application site covering.

6. The dressing of claim 1, wherein the application site covering is a drape made from a film including a porous or perforated area, and the oxygen scavenger is coupled to an outer surface of the drape within the porous or perforated area.

7. The dressing of claim 6, further comprising a gasket disposed beneath a skin-facing surface of the drape, wherein the porous or perforated area of the drape is confined within an area bound by the gasket beneath the drape.

8. The dressing of claim 7, wherein the oxygen scavenger is a component of a top assembly that covers the porous or perforated area of the drape when applied and adhered to the drape.

9. The dressing of claim 8, wherein the oxygen scavenger is packaged in an active state within a sealed package so to have depleted the oxygen in the sealed package before being applied and adhered to the drape.

10. The dressing of claim 1, wherein the wicking material includes air voids and 40 mmHg of external pressure on the wicking material compresses an air volume of the wicking material by at least 13%.

11. The dressing of claim 1, wherein the wicking material includes air voids making up at least about 60% of an overall volume of the wicking material.

12. The dressing of claim 1, wherein the wicking material includes air voids making up at least about 80% of an overall volume of the wicking material.

13. The dressing of claim 1, wherein the application site covering is silicone.

14. The dressing of claim 13, wherein the silicone is provided with a cavity and the oxygen scavenger is positioned within the cavity.

15. A packaged article comprising:
the dressing of claim 1; and
a sealed package in which the dressing is sealed, the sealed package inhibiting ambient oxygen from reacting with the oxygen scavenger until after the dressing has been removed from the sealed package.

16. A dressing comprising:
an application site covering; and
an oxygen scavenger provided with or positioned with respect to the application site covering so as to remove oxygen from a volume beneath the application site covering and around an application site covered by the application site covering, the application site covering and the oxygen scavenger being configured to maintain gas pressure beneath the application site covering around the application site that is above a therapeutic negative pressure while the oxygen scavenger is consuming oxygen beneath the application site covering, wherein the oxygen scavenger includes a reducing agent provided on a reducing agent substrate and an electrolyte solution provided in a rupturable package.

17. The dressing of claim 16, wherein the application site covering is a drape made from a film, and further comprising protuberances beneath a skin-facing surface of the drape for rupturing the rupturable package.

18. A dressing comprising:
an application site covering; and
an oxygen scavenger provided with or positioned with respect to the application site covering so as to remove oxygen from a volume beneath the application site covering and around an application site covered by the application site covering, the application site covering and the oxygen scavenger being configured to maintain gas pressure beneath the application site covering around the application site that is above a therapeutic negative pressure while the oxygen scavenger is consuming oxygen beneath the application site covering, wherein the oxygen scavenger includes a reducing agent dry electrolyte provided on a substrate and solvent water provided in a rupturable package.

* * * * *